United States Patent [19]

Darling

[11] 4,356,291

[45] Oct. 26, 1982

[54] PURIFICATION AND POLYMERIZATION OF HEXAFLUOROPROPYLENE OXIDE

[75] Inventor: Thomas R. Darling, Wilmington, Del.

[73] Assignee: E. I. Du Pont de Nemours and Company, Wilmington, Del.

[21] Appl. No.: 250,905

[22] Filed: Apr. 3, 1981

[51] Int. Cl.$^3$ .............................................. C08G 65/22
[52] U.S. Cl. ................................. 525/403; 260/544 F; 525/408; 528/26; 528/70; 528/341; 528/402; 560/180; 560/187; 562/583; 562/586; 564/143; 564/201; 564/505; 568/615
[58] Field of Search ................. 528/402, 26, 70, 341; 525/403, 408; 260/544 F; 560/180, 187; 562/583, 586; 564/143, 201, 505; 568/615

[56] References Cited

U.S. PATENT DOCUMENTS

| 3,242,218 | 3/1966 | Miller | 260/615 |
|---|---|---|---|
| 3,250,807 | 5/1966 | Fritz et al. | 260/535 |
| 3,250,808 | 5/1966 | Moore et al. | 260/535 |
| 3,342,875 | 9/1967 | Selman et al. | 260/615 |
| 3,412,148 | 11/1968 | Arbogast | 260/544 |
| 3,555,100 | 1/1971 | Garth et al. | 260/615 |
| 3,595,925 | 7/1971 | Garth | 260/615 |
| 3,600,409 | 8/1971 | Milian et al. | 260/348.5 |
| 3,660,315 | 5/1972 | Mill et al. | 260/2 A |
| 3,681,292 | 8/1972 | Loudas et al. | 260/77.5 NC |
| 3,733,349 | 5/1973 | Loudas et al. | 260/453 AL |
| 4,102,872 | 7/1978 | Griffin | 528/362 |
| 4,140,727 | 2/1979 | Cochoy et al. | 260/827 |
| 4,142,037 | 2/1979 | Evers et al. | 528/210 |

OTHER PUBLICATIONS

Rosser et al., Journal of Polymer Science, Polymer Letters, Edition, 18, pp. 135–139 (1980) "Synthesis of Perfluoroalkylether Triazine Elastomers".
Graham, Rubber Age, Aug. 1969, pp. 43–50, "Triazine Elastomer Vulcanizates".
Hill et al., ACS Symposium Series 59, "Anionic Polymerization of Fluorocarbon Epoxides," pp. 269–284 (1977).
Paciorek et al., Journal of Fluorine Chemistry 10, pp. 119–129 (1977).
Dorfman, et al., Die Angewandte Makromolekulare Chemie 16/17, pp. 75–82 (1971).

Primary Examiner—Earl A. Nielsen

[57] ABSTRACT

Purified hexafluoropropylene oxide is produced by scrubbing to remove impurities that inhibit polymerization of hexafluoropropylene oxide, thus permitting the preparation of polymers having a degree of polymerization of more than 200, including end-capped and chain-extended derivatives thereof.

22 Claims, No Drawings

PURIFICATION AND POLYMERIZATION OF HEXAFLUOROPROPYLENE OXIDE

TECHNICAL FIELD

This invention relates to a method of purifying hexafluoropropylene oxide, to the purified product that results from that method, to the process of homopolymerization of said purified hexafluoropropylene oxide, to the high molecular weight polymers that result from such homopolymerization, to the process of end-capping such high molecular weight polymers and the products that result from such process; and to the process of chain extending such high molecular weight polymers and the products that result from such process. The high molecular weight polymers of hexafluoropropylene oxide, including the end-capped and chain-extended derivatives thereof, are useful, depending on the molecular weight and various physical characteristics, as high performance elastomers, viscosity improvers for synthetic lubricants, or building blocks for preparing such viscosity improvers and high performance elastomers.

BACKGROUND ART

U.S. Pat. No. 3,600,409, granted Aug. 17, 1971 to Milian et al., discloses an improved process for synthesis of hexafluoropropylene oxide by oxidation of hexafluoropropylene. However, hexafluoropropylene oxide produced by this process or by any other current commercially available process results in a product containing certain impurities and by-products, including unreacted hexafluoropropylene, hexafluoroacetone, perfluoroacetyl fluoride, perfluoropropionyl fluoride, hydrogen fluoride, and water.

U.S. Pat. No. 3,412,148, granted Nov. 19, 1968 to Arbogast, discloses an improved process for polymerizing hexafluoropropylene oxide to give polymers having an average molecular weight of at least about 5500. Arbogast does recognize the importance of starting with dry monomer, suggests the use of a molecular sieve, and does achieve significant improvement in the degree of polymerization. However, Arbogast fails to recognize the significance of other key impurities generally present in commercially available hexafluoropropylene oxide monomer or formed during the preparation for polymerization.

U.S. Pat. No. 3,660,315, granted May 2, 1972 to Hill et al., discloses a further improved process for polymerizing hexafluoropropylene oxide to give substantially pure difunctional polymer where the degree of polymerization is up to about 50. However, like Arbogast, Hill et al. fail to recognize the significance of key impurities found or formed in commercially available hexafluoropropylene oxide monomer and the effect of such impurities on limiting the maximum degree of polymerization.

U.S. Pat. No. 3,250,808, granted May 10, 1966 to Moore et al., discloses monofunctional polymers of hexafluoropropylene oxide having a degree of polymerization of up to 100. However, like Arbogast and Hill, Moore et al. fail to recognize the significance of key impurities and the effect of such impurities on limiting the maximum degree of polymerization.

DISCLOSURE OF THE INVENTION

This invention relates to a method of purifying hexafluoropropylene oxide and to the purified product that results from that method. It has been discovered that the polymerization of hexafluoropropylene oxide is inhibited or halted by the presence of certain impurities which are commonly found in commercially available hexafluoropropylene oxide or which are formed during said polymerization or which are formed even during storage of the commercially available hexafluoropropylene oxide. The presence of even very small quantities of these impurities effectively limits the maximum degree of polymerization of hexafluoropropylene oxide, whether the polymerization be homopolymerization or copolymerization, but especially the former.

Hexafluoropropylene oxide is manufactured by oxidation of hexafluoropropylene. Typical supplies contain several trace impurities including up to 1% hexafluoropropylene, 0.01–0.05% carbon dioxide, 0–0.01% nitrogen, and 0–0.1% HFA (hexafluoroacetone). In addition, manufacturing specifications permit greater quantities of each of these impurities as well as up to 0.2% of other miscellaneous impurities. The miscellaneous impurities include materials such as perfluoroacetyl fluoride, carbonyl fluoride and perfluoropropionyl fluoride. These acid fluorides as well as hexafluoroacetone act as chain transfer agents in the polymerization of HFPO. While there are no specifications for the presence of $H_2O$, and HF has not been heretofore recognized as an impurity in commercially available HFPO, water is a transient and reactive impurity which will rapidly hydrolyze acid fluoride impurities as well as react slowly with hexafluoropropylene monomer itself. Both of these reactions produce additional hydrogen fluoride as well as the corresponding fluorocarbon acids.

Determination of the HF content in five typical HFPO supply cylinders shows hydrogen fluoride levels to be 23, 23, 28, 28 and 11 volume parts per million, respectively.

The Arbogast patent discussed above teaches the use of molecular sieves to remove water from HFPO monomer supplies, but no mention is made of hydrogen fluoride contamination. Molecular sieves function to remove water, but also slowly rearrange hexafluoropropylene oxide to perfluoropropionyl fluoride or hexafluoroacetone. Moreover, any acid fluorides present are readily hydrolyzed by the water of hydration on the molecular sieves to produce the free acids and additional hydrogen fluoride. The presence of free acids, hexafluoroacetone, perfluoropropionyl fluoride and the lower acid fluorides as well as the hydrogen fluoride profoundly affect the ability to polymerize hexafluoropropylene oxide to high molecular weight polymer. One of the most important aspects of the present invention was the recognition of the limiting effect exerted by several key trace impurities and the development of a relatively simple process for removing such trace impurities. It has been found that hexafluoropropylene oxide monomer suitable for preparation of high molecular weight polymer should contain less than 0.1 ppm hydrogen fluoride, less than 0.2% acid fluorides, less than 0.01% hexafluoroacetone and less than 1 ppm water. It should be noted that 1 ppm represents the limit of detection for water, but that as a practical matter water should, and will by the present invention, be eliminated down to less than 0.1 ppm, the same level as hydrogen fluoride. If water is present at levels greater than 0.1 ppm, it will react with any monomer or acid fluorides present prior to or during polymerization or alkoxides present during the polymerization to create hydrogen fluoride at levels above 0.1 ppm. Monomer of the required purity is conveniently prepared by passing commercially available hexafluoropropylene oxide monomer through a scrubber system, which can be varied depending on the quantity and type of impurities in the commercially available monomer. For example, if the monomer does not contain large quantities of acid fluorides, a single scrubbing of the monomer with metal hydride, e.g., calcium hydride or lithium aluminum hydride, will remove sufficient hydrogen fluoride and water to satisfy the requirements stated above and to be useful in preparing high molecular weight polymer. Calcium hydride is the preferred metal hydride for this scrubbing.

Preferably, the purified monomer of the present invention is prepared by passing commercially available hexafluoropropylene oxide monomer through a sequence of two scrubbers, the first containing an alkali metal or alkaline earth metal hydroxide and the second containing a metal hydride as described above. In the first stage, potassium hydroxide is preferred, although calcium, lithium, sodium and magnesium hydroxides will all perform satisfactorily. This first stage metal hydroxide scrub will effectively remove hydrogen fluoride, low molecular weight acid fluorides and hexafluoroacetone. Any water produced during the first scrubbing stage as well as any impurities remaining in the monomer stream will be effectively removed in the second metal hydride scrub. Any hydrogen produced in the second scrubbing stage will not adversely affect the polymerization of the purified hexafluoropropylene oxide monomer.

A typical laboratory scale alkali scrubber will consist of a glass tube approximately 12 inches in length by 2½" in diameter filled with reagent grade potassium hydroxide pellets. Typically, reagent grade is 85% by weight potassium hydroxide, most of the balance of which is water. A typical lab scale hydride scrubber in line behind the KOH scrubber will consist of a smaller glass tube approximately 1" in diameter and 10 inches long filled with small chunk reagent grade hydride. Particle size is typically ⅛". Monomer can be taken directly from the supply cylinder through a 2-stage pressure regulator and through a sequence of rotameters to calibrate and monitor flow rate. It is important not to use a molecular sieve column as a pre-dryer because this will cause formation of rearrangement and hydrolysis products in the monomer stream above those levels initially found in typical HFPO supply cylinders. The monomer can be taken directly from the rotameters through KOH and calcium hydride scrubbers and then preferably directly into the polymerization reactor. Typical flow rates and quantities of gas passed through the scrubber system as described are up to 100 milliliters per minute for a total of approximately 400 grams, respectively. Monomer so treated will have the required purity with respect to the four key impurities as discussed above. Of course, physical dimensions of the apparatus described can be altered and scaled up for commercial use without departing from the present invention.

Polymerization of the purified hexafluoropropylene oxide into high molecular weight polymer of the formula:

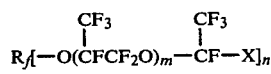

where X is COF, $R_f$ is the initiator residue, m is an integer greater than 200 and n is 1 or 2, requires, among other things, an initiator which may be monofunctional or difunctional depending on the desired polymerization product. Monofunctional initiator, a process for making monofunctional initiator, and a process of polymerizing hexafluoropropylene oxide using monofunctional initiator are disclosed in detail in U.S. Pat. No. 3,250,808, granted May 10, 1966 to Moore et al, the subject matter of which is hereby incorporated herein by reference. Preferred monofunctional initiator, a process for making such initiator, and a process for polymerizing hexafluoropropylene oxides with such monofunctional initiator are disclosed in U.S. Pat. No. 3,412,148, granted Nov. 19, 1968 to Arbogast, the subject matter of which is hereby incorporated herein by reference. In any event, preparation of the initiator is preferably carried out immediately prior to polymerization of the hexafluoropropylene oxide. Long term storage of the initiator can result in side reactions and by-products which will inhibit the preparation of high molecular weight polymers of hexafluoropropylene oxide.

Difunctional initiator, a process for making difunctional initiator, and a process of polymerizing hexafluoropropylene oxide using difunctional initiator are described in detail in U.S. Pat. No. 3,256,807, granted May 10, 1966 to Fritz et al., the subject matter of which is hereby incorporated herein by reference. Preferred difunctional initiator, a process for making such initiator, and a process for polymerizing hexafluoropropylene oxide with such difunctional initiator are disclosed in U.S. Pat. No. 3,660,315, granted May 2, 1972 to Hill et al., the subject matter of which is hereby incorporated herein by reference.

During the process of polymerization by addition of hexafluoropropylene oxide to the preformed initiator solution, it is preferred to add an inert organic liquid diluent in order to moderate the large increase in viscosity of the polymerizing mixture as the molecular weight of the polymer increases. Suitable diluents are fluids which are solvents for the polymer at the temperature of the polymerization reaction and which undergo no harmful reaction with the other ingredients in the polymerization zone. The most preferred diluents are hexafluoropropylene and dimers and trimers thereof. When a liquid diluent is used it is most preferred, and beyond what is disclosed in the subject matter incorporated by reference herein, that the addition of monomer and diluent be balanced so as to maintain the reaction mass as a single liquid phase. This balance can be achieved by periodic addition of monomer and diluent or by continuous addition of each at appropriate rates. Maintenance of the balance to avoid creating a second liquid phase is especially important during the early stages of the addition of monomer, i.e., when the forming polymer is of low molecular weight and the solvent for the initiator (e.g., tetraglyme) constitutes a larger part of the reaction mass. If diluent is added too rapidly or in too large an amount, it does not comletely dissolve the reaction mass and forms a separate phase. This condition leads to an increase in chain transfer in the polymerization, a reduction in the maximum molecular weight which can be achieved in a given polymerization, and a reduction of functionality in the polymer obtained in the case of preparation of difunctional polymer.

Polymer produced by the process of the present invention will be of high molecular weight, i.e., the number average degree of polymerization will be at least about 200, and will include polymers where the number average degree of polymerization will be as high as 600 or more. The particular degree of polymerization (or molecular weight) that can be achieved by the process of the present invention will depend on a variety of factors including: purity of monomer, the ratio between the quantity of initiator and the quantity of monomer, the functionality of the initiator, the number of liquid phases in the reaction mixture, and the maintenance of the integrity of the reaction system.

Depending on the particular desired end use, high molecular weight polymer of the present invention may be end-capped and/or chain extended. For example, hydrogen or fluorine end-capping can be used to make the polymer more thermally and hydrolytically stable. Other types of end-capping can be used to provide reactive sites for further reaction, e.g., chain extension. The high molecular weight polymers of the present invention can be end-capped, i.e., the polymers of the present invention where X is COF can be converted to polymers in which the COF group is replaced with any one or more of the following groups:
—COOR, —CONR$_2$, —H, —F, —CN, —Br, —I, —CH$_2$OH, —CH$_2$NR$_2$, —COO$^-$M$^+$, —CF$_2$—O—CF$_2$CF$_2$I, or —C(CH$_3$)$_2$OH
where R=hydrogen, alkyl, aryl or cycloalkyl and M$^+$ is a mono-, di-, tri-, or tetra- valent metal ion. Preferred polymers of the present invention include those which have been end-capped with one or more of the following groups: —COOH, —H, —F, —Br, —I, —CN, —COO$^-$M$^+$ or —CF$_2$—O—CF$_2$CF$_2$I.

Fluorine end-capping can be accomplished by hydrolyzing the acid fluoride terminated polymer and then simultaneously fluorinating and decarboxylating the hydrolyzed product, e.g., as disclosed in U.S. Pat. No. 3,242,218, granted Mar. 22, 1966 to Miller, U.S. Pat. No. 3,595,925, granted July 27, 1971 to Garth, and U.S. Pat. No. 3,555,100, granted Jan. 12, 1971 to Garth. Bromine and iodine end-capping can be achieved by the Hunsdieker reaction of the appropriate halogen with the silver salt of the carboxylic acid terminated polymer, e.g., as disclosed in U.S. Pat. No. 4,085,137. End-capping with —CH$_2$OH can be achieved by reaction of carboxylic acid terpolymer with lithium aluminum hydride, e.g., as disclosed in U.S. Pat. No. 4,085,137. Hydrogen end-capping can be accomplished by pyrolysis of a hydrogen containing derivative of the acid fluoride terminated polymer, or by reacting a monovalent metal acid salt of the acid fluoride terminated polymer with a solvent containing an active hydrogen, as described in U.S. Pat. No. 3,342,875, granted Sept. 19, 1967 to Selman et al. Acid group end-capping can be accomplished by hydrolyzing the acid fluoride terminated polymer; ester group end-capping can be accomplished by reacting the acid fluoride terminated polymer with an alcohol; amide group end-capping can be accomplished by reacting the acid fluoride terminated polymer with ammonia or an amine; the amide end group can be converted to a —CH$_2$NH$_2$ end group by reaction with lithium aluminum hydride, e.g., as disclosed in U.S. Pat. No. 4,080,319; nitrile group end-capping can be accomplished by dehydrating the amide end-capped polymer; the —CF$_2$OCF$_2$CF$_2$I end group can be obtained by reaction of the acid fluoride terminated polymer with a mixture of CF$_2$=CF$_2$, KF and I$_2$ or ICl, e.g., as disclosed in *J. Org. Chem.*, 33, 1839 (1968); the —C(CF$_3$)$_2$OH end group can be obtained by reaction of the acid fluoride terminated polymer with methyl magnesium halides, e.g., as disclosed in U.S. Pat. No. 4,140,727; and acid salt group end-capping can be accomplished by mixing the acid end-capped polymer with an aqueous dispersion of a metal hydroxide or metal oxide, e.g., all as described in U.S. Pat. No. 3,660,315, granted May 2, 1972 to Hill et al.

Chain extension of the high molecular weight polymers of the present invention may also be desirable and can be accomplished by conventional techniques, including those disclosed in U.S. Pat. No. 4,142,037, granted Feb. 27, 1979 to Evers et al., U.S. Pat. No. 4,102,872, granted July 25, 1978 to Griffin, U.S. Pat. No. 4,140,727, granted Feb. 20, 1979 to Cochoy et al., U.S. Pat. No. 3,681,292, granted Aug. 1, 1972 to Loudas et al., U.S. Pat. No. 4,085,137, U.S. Pat. No. 3,733,349, Air Force Materials Laboratory Technical Report No. AFML-TR-75-86, Part II (1976) (Air Force Systems Command, Wright-Patterson Air Force Base, Ohio) *Journal of Fluorine Chemistry*, Vol. 10, pp. 119–129 (1977); *Die Angewandte Makromolekulare Chemie*, Vol. 16/17, pp. 75–82 (1971); *Rubber Age*, August 1969, pp. 43–50; and *Journal of Polymer Science, Polymer Letters Edition*, Vol. 18, pp. 135–139 (1980). Compounds which can be used to effectively chain extend the high molecular weight polymers of the present invention include di- or tri-functional agents such as glycols and polyamines. In addition, the polymers of the present invention can be linked via various coupling moieties, including benzoxazole, triazine, isoxazole, oxadiazole, siloxane, di- or tri-urethane, di-imide, cyanurate, and di- or tri-amide. Preferred coupling moieties include benzoxazole, triazine, isoxazole, oxadiazole, siloxane and cyanurate.

In addition to the conventional end-capping and chain extension techniques described and discussed above, the polymers of the present invention which are carboxyl terminated can be treated with metal bases such as sodium, calcium, magnesium or zinc hydroxides or oxides. The metal ion serves as a chain extender, but unlike conventional chain extension, this form is thermally reversible, thus having the general character of an ionomer. Certain metal oxides, such as mercuric oxide, will chain extend in a fashion similar to the ionomers mentioned above, but when heated, there are formed covalently bonded chains which are no longer thermally reversible (see e.g., U.S. Pat. No. 3,515,701, granted 1970 to Tiers). The most preferred of the metal hydroxides and oxides is mercuric oxide.

In the following examples of specific embodiments of the present invention, parts and percentages are by weight and temperatures are in degrees Celsius unless otherwise specified. Measurements not originally in SI units have been so converted and rounded where appropriate.

EXAMPLE 1

Preparation of Monofunctional Initiator

A monofunctional initiator solution was prepared by reacting 2.09 grams of effectively dried (according to procedures described in U.S. Pat. No. 3,660,315) high purity cesium fluoride with 10.1 grams of perfluorinated acid fluoride, which was an oligomer of HFPO with a number average molecular weight of 845 and an average degree of polymerization of approximately 5 (prepared according to procedures described in U.S. Pat. No. 3,412,148). The cesium fluoride and the acid fluoride were reacted in a Pyrex shaker tube containing six grams of tetraglyme which had been freshly distilled from lithium aluminum hydride. Strictly anhydrous procedures were observed throughout. The mixture was shaken for 6 hours to assure complete reaction. Excess cesium fluoride was driven to the bottom of the tube by centrifugation. The clear, liquid initiator contained approximately 4 millimoles of active cesium alkoxide per milliliter.

EXAMPLE 2

Preparation of Monofunctional Polyhexafluoropropylene Oxide

The polymerization vessel consisted of a fully glass jacketed four-neck round bottom reactor which is equipped with a paddle stirrer, reflux condenser cooled with solid carbon dioxide, gas inlet port and a thermocouple well. The entire reactor was dried thoroughly at 200° C. in a dry nitrogen atmosphere and was assembled and kept dry with a blanket of high purity dry nitrogen. Methanol was used as a coolant and was pumped through the coolant jacket from a Neslab ULT80 low temperature circulator and refrigerator system. With the reactor at room temperature 4 milliliters of initiator prepared as in Example 1 was introduced by means of syringe and the reactor was cooled to an internal temperature of between −30° to −34° C. Liquified hexafluoropropylene was used as a solvent to dilute the cold viscous initiator solution. The addition rate for the hexafluoropropylene was 1 gram per minute for a total of 20 grams. With slow stirring, purified hexafluoropropylene oxide purified in a two-stage (potassium hydroxide/calcium hydride) scrubber as described above was added as a gas in a semi-batch fashion at a rate of 11 milliliters per minute for a period of 20 hours. Throughout the reaction period the polymer mixture appeared as a clear and increasingly viscous liquid. Toward the end of the addition period the solution became extremely difficult to stir effectively and a further dilution with additional hexafluoropropylene was necessary. The reaction mixture was allowed to stand for approximately two hours to consume unreacted hexafluoropropylene oxide. 20 grams of hexafluoropropylene was added to the reactor at a rate of 1 gram per minute. The reaction mixture became less viscous and remained clear and could be effectively stirred. The addition of hexafluoropropylene oxide was resumed at the same rate of 11 milliliters per minute. At the end of 21 hours the reaction mixture had once again become very viscous and very difficult to stir effectively. The monomer feed was stopped and the reactor was allowed to stand for an additional three hours to assure complete reaction with residual hexafluoropropylene oxide. A vacuum was applied to the reactor to remove the hexafluoropropylene diluent at low temperature. Once most of the hexafluoropropylene was removed the reactor was slowly warmed to room temperature. The extremely viscous and frothy polymer was stirred slowly with a paddle stirrer to remove the last traces of diluent. The polymer had a tendency to climb the shaft of the reactor stirrer but would flow back down into the reactor upon further warming of the polymer. Warm polymer was removed from the reactor under anhydrous conditions to preserve the acid fluoride end group. Quantitative infrared analysis on the acid fluoride end group indicated a number average molecular weight of approximately 50,000. This corresponds to a number average degree of polymerization of approximately 300. As confirmation of the acid fluoride end group analysis the polymer was converted to the methyl ester by treatment with absolute methanol. Quantitative IR end group analysis on the methyl ester also indicated a number average molecular weight in the range of 50,000. Hexafluoropropylene oxide monomer conversion was 100% as indicated by the mass balance between monomer fed and polymer isolated.

EXAMPLE 3

Polymerization of HFPO with Difunctional Initiator

The polymerization was carried out as in Example 2 but with the following modifications: The initiator solution was prepared by adding, under nitrogen, 7.50 grams (0.0337 mole) of tetraglyme to 2.11 grams (0.0139 mole) of anhydrous cesium fluoride and then adding 2.77 grams (0.0065 mole) of a compound of the formula:

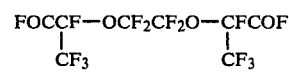

i.e., 2,2′-[(tetrafluoroethylene)dioxy]bis(tetrafluoropropionyl fluoride). The mixture was shaken for 24 hours at room temperature and then was centrifuged to remove unreacted cesium fluoride. Then 4.0 milliliters of the solution (0.0027 mole of initiator) was added to the reactor at room temperature. The polymerization was carried out at −32° to −39° C. using the following monomer addition schedule:

| Addition Time, Hrs. | g HFP added | g HFPO added |
|---|---|---|
| 0.33 | 20 | |
| 20.0 | | 123 |
| 0.33 | 20 | |
| 19.5 | | 120 |
| Total | 40 g | 243 g |

The polymer was worked up as in Example 2. There was obtained 243 grams of acid fluoride end group polymer with inherent viscosity of 0.104 dl/g (number average DP=260).

EXAMPLE 4

Hydrogen End-Capping of Poly-HFPO Prepared with Difunctional Initiator

A 3-neck flask fitted with a stirrer, condenser and nitrogen bubbler was charged with 34 grams of polymer produced in Example 3, 3.4 milliliters of diethylene glycol and 3.4 milliliters of water containing 0.23 grams of KOH pellets (85% KOH). The mixture was stirred for 2.5 hours at 85°, giving a stiff marshmallow-like dispersion. After stirring at 175° for 6 hours, two separate phases had formed. The lower fluorocarbon phase was diluted with 70 milliliters of $CF_2ClCFCl_2$ and was washed with water, dilute HCl and again with water. Removal of solvent under vacuum at 200° gave 26.1 grams of hydrogen end-capped polymer, inherent viscosity=0.082 dl/g, membrane osmometry number average molecular weight 43,500 (number average DP=260).

EXAMPLE 5

Polymerization of HFPO with Difunctional Initiator

The polymerization was carried out as in Example 3 but with the following modifications: The initiator solution was prepared by adding, under nitrogen, 7.95 grams (7.8 milliliters, 0.0358 mole) of tetraglyme to 2.54 grams (0.0167 mole) of cesium fluoride and then adding 2.91 grams (1.75 milliliters, 0.0068 mole) of the initiator used in Example 3. The mixture was shaken overnight at room temperature and was then centrifuged for 30 minutes to remove unreacted cesium fluoride. Then 4.0 milliliters of the solution (0.00286 mole initiator) was added to the reactor at room temperature. The polymerization was carried out at −32° to −34° C. using the following monomer addition schedule.

| Addition Time, Hrs. | g HFP added | g HFPO added |
|---|---|---|
| 0.23 | 7.0 | |
| 2.67 | | 15.2 |
| 0.77 | 23.0 | |
| 8.25 | | 47.0 |
| 0.50 | 15.0 | |
| 24.3 | | 175.6 |
| 0.50 | 15.0 | |
| 9.0 | | 65.1 |
| 0.9 | 26.0 | |
| 28.0 | | 202.4 |
| Total | 86 g | 505 g |

The polymer was worked up as in Example 2. There was obtained 505 grams of polymer with inherent viscosity of 0.162 dl/g. The hydrogen end-capped polymer was prepared as in Example 4 and had inherent viscosity of 0.127 dl/g and a membrane osmometry number average molecular weight of 73,900 (number average DP=445).

EXAMPLE 6

Fluorine End-Capping of Poly-HFPO

One hundred fifteen grams of carboxylic acid end group poly-HFPO, obtained by hydrolysis of difunctional acid fluoride end group poly-HFPO, inherent viscosity, 0.099 dl/g, was extracted three times with a 100 milliliter portion of ether, stirring vigorously at room temperature under nitrogen, to remove most of the tetraglyme present. The polymer was then heated at 80° C./6.7 Pa for 5 hours to remove residual diethyl ether.

Eighty-four grams of the polymer was fluorinated in a 110 milliliter Hastelloy shaker tube in a barricade unit by pressuring to 1034 MPa with a 25/75 vol/vol $F_2/N_2$ mixture and then heating gradually to 140° C. during a one hour period and then holding at 140° C. for 4 hours. The 75 grams of recovered colorless product had no carbonyl absorption in the infrared. No C-H absorption could be detected in the FTIR spectrum. The inherent viscosity of the polymer was 0.094 dl/g, very similar to that (0.090 dl/g) of the hydrogen end-capped poly-HFPO derived from the same base polymer. Number-average molecular weight by membrane osmometry was 54,300. The fluorine end-capped polymer was shown to be an effective viscosity index improver for low molecular weight poly-HFPO synthetic lubricants.

EXAMPLE 7

Reaction of Difunctional Poly-HFPO with Ethylene Glycol

To 24.8 grams of acid fluoride end group p-HFPO, inherent viscosity 0.16 dl/g in Freon ® E3 fluorocarbon fluid at 30° C.; (Freon ® E3 is 2H-heptadecafluoro-5,8-bis(trifluoromethyl)-3,6,9-trioxadodecane), prepared as in Example 5 was added 13 l of ethylene glycol. The mixture was stirred under nitrogen and allowed to stand overnight. Then an additional 13 l of ethylene glycol was stirred in. After 24 hours the mixture was somewhat elastomeric. When the polymer was mixed with fumed silica it was converted to a resilient solid.

EXAMPLE 8

Calcium Ionomer of Difunctional Poly-HFPO

Forty grams of acid fluoride end group poly-HFPO prepared with difunctional initiator, having inherent viscosity of 0.16 dl/g, was dissolved in 40 milliliters of Freon ® E2 fluorocarbon fluid (i.e., 2H-tetradecafluoro-5-(trifluoromethyl)-3,6-dioxanonane) and warmed to 70° C. The solution was stirred with a solution of 0.30 grams (excess) $Ca(OH)_2$ in 6 milliliters water at 70° C. for 30 minutes and then at room temperature for 4 hours. A sample of the fluorocarbon solution was stirred 3 times with water, 3 times with Freon ® 113 (i.e., 1,1,2-trichlorotrifluoroethane) and 3 times with methanol, discarding all wash solutions. The precipitated polymer was dried overnight at room temperature under high vacuum. After mixing with Cab-O-Sil fumed silica the polymer was rolled into a ball which bounced.

The bulk of the polymer was isolated several months later, after prolonged contact with $Ca(OH)_2$ solution, by washing with water, acetone, Freon ® 113 and methanol. The precipitated polymer was dried overnight at 85° C. under reduced pressure, leaving a rubbery polymer which was pressed into a resilient elastomeric film.

EXAMPLE 9

Chain Extension of Poly-HFPO with Ethylene Diamine

To 3.54 grams of a "difunctional" acid fluoride end group poly-HFPO, inh=0.17 dl/g, was added 0.011 grams (excess) of ethylene diamine under nitrogen. The mixture was stirred at room temperature and allowed to stand in a closed container for 1.75 hours. At this time the polymer had turned yellow and the inherent viscosity had increased to 0.22 dl/g. After standing overnight the polymer was stiff and rubbery.

I claim:

1. A polymer of hexafluoropropylene oxide of the formula

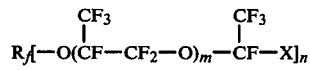

wherein
X is COF, COOR, $CONR_2$, H, F, CN, Br, I, $CH_2OH$, $CH_2NR_2$, $C(CH_3)_2OH$, $COO^-M^+$, or $CF_2-O-CF_2CF_2I$,
R is hydrogen, alkyl, aryl, or cycloalkyl,
$M^+$ is a mono-, di-, tri- or tetra-valent metal ion, $R_f$ is the initiator residue and can be monofunctional or difunctional, m is an integer greater than 200, and n is 1 if $R_f$ is monofunctional and 2 if $R_f$ is difunctional.

2. A polymer of claim 1 wherein X is COF.

3. A process of preparing a polymer of claim 2 which comprises reacting purified hexafluoropropylene oxide containing less than 0.1 ppm hydrogen fluoride, less than 0.2% acid fluorides, less than 0.01% hexafluoroacetone and less than 1 ppm water with an alkali metal perfluoroalkoxide polymerization initiator.

4. The process of claim 3 wherein the initiator is difunctional.

5. The process of claim 4 wherein the initiator is a compound of the formula:

$$Cs^+{}^-OCF_2CFOCF_2CF_2OCFCF_2O^-Cs^+$$
$$\phantom{Cs^+{}^-OCF_2}|\phantom{CFOCF_2CF_2OC}|$$
$$\phantom{Cs^+{}^-OCF_2}CF_3\phantom{OCF_2CF_2O}CF_3$$

6. The process of claim 3 wherein the reaction mixture is maintained as a single phase.

7. The process of claim 5 wherein the reaction mixture is maintained as a single phase.

8. A polymer of claim 1 wherein X is COOR, $CONR_2$, H, F, Br, I, CN, $CH_2OH$, $CH_2NR_2$, $C(CH_3)_2OH$, $COO^-M^+$, or $CF_2-O-CF_2CF_2I$.

9. A polymer of claim 5 wherein X is COOH, H, F, Br, I, CN, $COO^-M^+$, or $CF_2-O-CF_2CF_2I$.

10. A process of preparing a polymer of claim 1 where X is F comprising hydrolyzing the corresponding polymer where X is COF, and then simultaneously halogenating and decarboxylating the hydrolyzed product.

11. A process for preparing a polymer of claim 1 where X is H comprising pyrolysis of a hydrogen containing derivative of the corresponding polymer where X is COF.

12. A process of preparing a polymer of claim 1 where X is H comprising reacting a monovalent metal acid salt of the corresponding polymer where X is COF with a solvent containing an active hydrogen.

13. A process of preparing a polymer of claim 1 where X is COOR and R is hydrogen comprising hydrolyzing the corresponding polymer where X is COF.

14. A process of preparing a polymer of claim 1 where X is CN comprising dehydrating the corresponding polymer where X is $CONH_2$.

15. A process of preparing a polymer of claim 1 where X is $COO^-M^+$ comprising mixing the corresponding polymer where X is COOH with an aqueous dispersion of a metal hydroxide or metal oxide.

16. A process of preparing a polymer of claim 1 where X is Br comprising reacting the silver acid salt of the corresponding polymer with bromine.

17. A process of preparing a polymer of claim 1 where X is I comprising reacting the silver acid salt of the corresponding polymer with iodine.

18. A process of preparing a polymer of claim 1 where X is $CF_2-O-CF_2-CF_2I$ comprising reacting the corresponding acid fluoride end-capped polymer with a mixture of tetrafluoroethylene, potassium fluoride and a compound selected from the group consisting of iodine and iodine chloride.

19. Chain-extended polymers of claim 1.

20. A polymer of claim 19 wherein the chain extension agent is selected from the group consisting of glycols, polyamines, metal hydroxides and metal oxides.

21. A polymer of claim 19 wherein the coupling moiety is selected from the group consisting of benzoxazole, triazine, isoxazole, oxadiazole, siloxane, diurethane, triurethane, diimide, cyanurate, diamide, triamide.

22. A polymer of claim 19 wherein the coupling moiety is a carbon-carbon covalent bond joining polymer segments of the formula $$R_f\!-\!O(CF-CF_2-O)_m-CF\!\!\frac{}{n}-$$
$$\phantom{R_f\!-\!O(}|\phantom{F-CF_2-O)_m-}|$$
$$\phantom{R_f\!-\!O(}CF_3\phantom{-CF_2-O)_m-}CF_3$$

where $R_f$ is the initiator residue and can be monofunctional or difunctional, m is an integer greater than 200, and n is 1 if $R_f$ is monofunctional and 2 if $R_f$ is difunctional.

* * * * *

UNITED STATES PATENT OFFICE
CERTIFICATE OF CORRECTION

PATENT NO. : 4,356,291
DATED : October 26, 1982
INVENTOR(S) : Thomas Robert Darling It is certified that error appears in the above-identified patent and that said Letters Patent are hereby corrected as shown below:

At Column 11, line 31 (i.e. Claim 9, line 9)

"5" should be --1--.

Signed and Sealed this

Eighteenth Day of January 1983

[SEAL]

Attest:

GERALD J. MOSSINGHOFF

Attesting Officer    Commissioner of Patents and Trademarks